US008987509B2

(12) United States Patent
Tolan et al.

(10) Patent No.: US 8,987,509 B2
(45) Date of Patent: Mar. 24, 2015

(54) RECOVERY OF VOLATILE CARBOXYLIC ACIDS BY EXTRACTIVE EVAPORATION

(75) Inventors: Jeffrey S. Tolan, Ontario (CA); Brian Foody, Ontario (CA); Vijay Anand, Ontario (CA); Daphne Wahnon, Ontario (CA)

(73) Assignee: Iogen Energy Corporation, Ontario (CA)

( * ) Notice: Subject to any disclaimer, the term of this patent is extended or adjusted under 35 U.S.C. 154(b) by 415 days.

(21) Appl. No.: 13/392,728

(22) PCT Filed: Aug. 18, 2010

(86) PCT No.: PCT/CA2010/001273
§ 371 (c)(1),
(2), (4) Date: May 7, 2012

(87) PCT Pub. No.: WO2011/022812
PCT Pub. Date: Mar. 3, 2011

(65) Prior Publication Data
US 2012/0215026 A1 Aug. 23, 2012

Related U.S. Application Data

(60) Provisional application No. 61/237,393, filed on Aug. 27, 2009.

(51) Int. Cl.
*C07C 51/44* (2006.01)
*B01D 3/38* (2006.01)
(Continued)

(52) U.S. Cl.
CPC ............... *B01D 3/02* (2013.01); *C07C 51/445* (2013.01); *C12F 3/00* (2013.01); *Y02E 50/16* (2013.01)
USPC .......................................... 562/512; 562/608

(58) Field of Classification Search
USPC .................................................. 562/512, 608
See application file for complete search history.

(56) References Cited

U.S. PATENT DOCUMENTS

| 114,517 | A | 5/1871 | Bell |
| 118,788 | A | 9/1871 | Burcey |

(Continued)

FOREIGN PATENT DOCUMENTS

| CN | 1944374 A | 4/2007 |
| CN | 101306989 B | 4/2011 |

(Continued)

OTHER PUBLICATIONS

Adams and Voorhees, Organic Syntheses, Coll. vol. p. 280 (1941); or vol. 1, p. 49 (1921).*

(Continued)

*Primary Examiner* — Brandon Fetterolf
*Assistant Examiner* — Janet L Coppins
(74) *Attorney, Agent, or Firm* — Fitzpatrick, Cella, Harper & Scinto

(57) ABSTRACT

A process for recovering a volatile carboxylic acid from an aqueous stream containing same comprising the steps of: (a) evaporating the aqueous stream to produce a vapour stream comprising the volatile carboxylic acid that has been vapourized and water vapour, which aqueous stream is produced by a conversion process using a lignocellulosic feedstock as a substrate; (b) contacting the vapour stream with an organic solvent so as to extract the volatile carboxylic acid present in the vapour stream, thereby producing a liquid stream comprising the organic solvent and the volatile carboxylic acid, and a water vapour stream, wherein the organic solvent has an atmospheric boiling point of at least about 150° C. and is insoluble in water; and (c) separating the volatile carboxylic acid from the organic solvent.

21 Claims, 1 Drawing Sheet

(51) Int. Cl.
    *B01D 3/02* (2006.01)
    *C12F 3/00* (2006.01)

(56) References Cited

U.S. PATENT DOCUMENTS

| | | | |
|---|---|---|---|
| 939,980 | A | 11/1909 | Chute |
| 998,234 | A | 7/1911 | Crossley et al. |
| 1,052,446 | A | 2/1913 | Volney |
| 1,192,987 | A | 8/1916 | Campbell |
| 1,314,765 | A | 9/1919 | Stone |
| 1,858,150 | A | 5/1932 | Gorhan |
| 1,993,259 | A | 3/1935 | Buc |
| 2,266,718 | A | 12/1941 | Bludworth |
| 2,444,527 | A | 7/1948 | Pomeroy |
| 2,471,942 | A | 5/1949 | Drew |
| 3,084,109 | A | 4/1963 | Ure et al. |
| 3,177,263 | A | 4/1965 | Francis |
| 3,490,997 | A | 1/1970 | Bumey et al. |
| 3,530,043 | A | 9/1970 | Horn |
| 3,530,044 | A | 9/1970 | Horn |
| 3,951,755 | A | 4/1976 | Sartorius et al. |
| 4,088,660 | A * | 5/1978 | Puurunen ............ 549/490 |
| 4,100,189 | A | 7/1978 | Mercier |
| 4,102,705 | A | 7/1978 | Pfeiffer et al. |
| 4,342,831 | A | 8/1982 | Faber et al. |
| 4,353,784 | A * | 10/1982 | Koga et al. ............ 203/16 |
| 4,396,463 | A | 8/1983 | Josis et al. |
| 4,401,514 | A | 8/1983 | Kanzler et al. |
| 4,898,644 | A | 2/1990 | Van Horn |
| 4,978,430 | A | 12/1990 | Nakagawa et al. |
| 5,162,214 | A | 11/1992 | Hubred |
| 5,175,357 | A | 12/1992 | Van Brunt |
| 5,264,623 | A | 11/1993 | Oehr et al. |
| 5,306,398 | A | 4/1994 | Seidel et al. |
| 5,399,751 | A | 3/1995 | Gentry et al. |
| 5,492,603 | A | 2/1996 | Gualy et al. |
| 6,662,780 | B2 | 12/2003 | Yook |
| 6,793,777 | B1 | 9/2004 | Rudinger et al. |
| 6,955,743 | B2 | 10/2005 | Rousu et al. |
| 7,048,835 | B2 | 5/2006 | Jang et al. |
| 7,196,218 | B2 | 3/2007 | Gaddy et al. |
| 2007/0068792 | A1 | 3/2007 | Jang et al. |

FOREIGN PATENT DOCUMENTS

| | | |
|---|---|---|
| EP | 1520847 | 4/2005 |
| GB | 774809 | 5/1957 |
| GB | 1407523 | 9/1975 |
| WO | 02/053829 | 7/2002 |
| WO | 03/074781 | 9/2003 |

OTHER PUBLICATIONS

E.L. Heric et al, Distribution of Acetic and Propionic Acids Between Furfural and Water, Journal of Chemical and Engineering Data, vol. 5, No. 3 (1960) 272-74.

E.L. Heric et al., Distribution of Burytic Acid between Furfural and Water at 25 degrees and 35 degrees celcius, Journal of Chemical and Engineering Data, vol. 11, No. 1 (1966) 38-40.

B. Schierbaum et al., Isolation of Carboxylic Acids from Aqueous Solutions by Extraction with Dialkylcarboxylic Amides/Trialkylamines, Chem. Eng. Tech., vol. 22 (1999) 37-41.

N.L. Ricker et al., Solvent Extraction with Amines for Recovery of Acetic Acid from Dilute Acqueous Industrial Streams, J. Separ. Proc. Technol. vol. 1, No. 2 (1980) 23-30.

K.J. Zeitsch, The Chemistry and Technology of Furfural and its Many By-Products, ACS Sugar Series, vol. 13, (2000) 111-13.

L. Lei et al., Separation of acetic acid and water by complex extractive distillation, Separation and Purification Technology, vol. 36 (2004) 131-38.

\* cited by examiner

US 8,987,509 B2

RECOVERY OF VOLATILE CARBOXYLIC ACIDS BY EXTRACTIVE EVAPORATION

This application is a national stage application of PCT/CA2010/001273 having an international filing date of Aug. 18, 2010, which claims benefit of U.S. provisional application No. 61/237,393 filed Aug. 27, 2009, both of which are incorporated by reference herein.

FIELD OF THE INVENTION

The present invention relates to a process for recovering carboxylic acids, more particularly volatile carboxylic acids from an aqueous stream.

BACKGROUND OF THE INVENTION

Carboxylic acids are valuable chemicals that are employed in many applications in industry. For example, acetic acid has a wide range of uses, including in the chemical industry to produce cellulose acetate, rayon acetate, acetic anhydride and plastics and in the food industry as a preservative. Acetic acid is produced both synthetically and by bacterial fermentation. Most of the acetic acid produced for the chemical industry is made by methanol carbonylation, whereby methanol and carbon monoxide are reacted to produce acetic acid. Acetic acid that is used as a food additive is produced by the biological route, as many nations' food purity laws stipulate that vinegar used in foods must be of biological origin. Other carboxylic acids of industrial importance include formic acid and propionic acid. Formic acid can react to form esters and is used as a preservative in animal feeds while propionic acid is the flavorant in Swiss cheese.

Recovering acetic acid that is produced as a byproduct from lignocellulosic conversion processes has received much attention in recent years. Agricultural wastes are of particular interest as they are inexpensive, and are often burned or landfilled. There is an enormous untapped potential for their use not only as a source of fermentable sugar to produce fuels such as ethanol or butanol, but also as a source of byproducts, such as acetic acid In the production of fermentable sugar from lignocellulosic feedstocks, the acetic acid arises from the hydrolysis of acetyl groups present on the hemicellulose and lignin components of the feedstock. For instance, the acetic acid may originate from an acid pretreatment, which is conducted to hydrolyze the hemicellulose component of the feedstock, but with limited hydrolysis of the cellulose. The cellulose is then hydrolyzed with cellulase enzymes and the glucose so produced is fermented to ethanol, butanol or other fermentation products. Other known methods for producing sugar hydrolyzate streams that also contain acetic acid or acetate salts include alkali pretreatment conducted under conditions that result in hemicellulose hydrolysis, followed by enzymatic hydrolysis of cellulose with cellulase enzymes or complete acid hydrolysis conducted in a single step under harsher conditions so that both the hemicellulose and cellulose present in the feedstock are hydrolyzed. Acetic acid can also be produced as a byproduct in other industries that utilize lignocellulosic materials as feedstocks, including during furfural production and in the pulp and paper industry.

Formic acid is also a byproduct produced during the pretreatment of lignocellulosic feedstocks, specifically by sugar and lignin degradation that occurs during such processes. Formic acid is also produced as a byproduct during furfural production from lignocellulosic feedstocks, along with acetic acid.

Whether or not the recovery of carboxylic acids from industrial process streams is feasible depends on the cost of the recovery, the ability to remove impurities and the ability to concentrate it to a sufficiently high concentration (e.g., in the case of acetic acid as glacial acetic acid). Streams derived from lignocellulosic feedstocks pose particular problems for successful recovery of carboxylic acids due to their multi-component nature and because the concentration of carboxylic acids in such streams is typically low.

Liquid-liquid extraction is a known technique for recovering carboxylic acids. This method, also known as solvent extraction, extracts carboxylic acids with a solvent or mixture of solvents to produce an extract containing the acid and the extracting solvent and typically some of the water in the process stream. The extract may be distilled to recover the extracting solvent for reuse in the process and to obtain a concentrated acid solution free of the solvent. Such extractions may involve the use of organic bases such as alkylamines and phosphine oxides. (See for example Ricker, N. L., Pittman, E. F., and King, C. J., J. Separ. Proc. Technol., 1980, 1(2):23-30).

However, the recovery of carboxylic acids by liquid-liquid extraction at the low concentrations found in process streams resulting from lignocellulosic conversion process, e.g., less than about 2% (w/w), requires significant amounts of the organic solvent in order for the extraction to be effective. This is a major disadvantage as such solvents are costly. Moreover, the solvent often has a high affinity for lignin and other high molecular weight compounds that are present in many of the streams produced during the conversion process. These compounds can accumulate in the solvent and render it less effective. Furthermore, the use of agitation to increase the rate of liquid-liquid extraction often leads to the formation of emulsions of droplets of the aqueous phase within the organic phase. The separation of the emulsified phases can be difficult. Accordingly, liquid-liquid extraction is not preferred for directly recovering acetic acid from streams containing these components.

British Patent No. 1,407,523 discloses a method of recovering acetic acid by extractive rectification. According to the method, a crude acid mixture containing acetic acid is fed into the lower half of a first rectification column either in liquid form or the form of a vapour. The extractant, 1,2-dimorpholylethane, is fed as a liquid in the upper third of the column. The sump product of the first column, which consists of an anhydrous mixture of acetic acid and extractant, is fed continuously to the lower half of the second rectification column. Acetic acid, which is free from water and extractant is taken off as distillate, while a product, consisting essentially of the extractant is obtained as a sump product. A similar process is disclosed by U.S. Pat. No. 3,951,755 (Sartorius et al.) using N-methyl acetamide as the extractant for acetic acid. CN101306989 discloses using a thiocyanate, acetate or nitrate salt in combination with an organic solvent for separating water and acetic acid by extractive distillation. Moreover, Lei et al. (Separation and Purification Technology, 2004, 36:131-138) discloses a "complex extractive distillation" for separating acetic acid and water using tributylamine as the separating agent. However, distillation is a very capital intensive process. Because of this, it is generally conceded as not being worthwhile for concentrating dilute aqueous acetic acid having less than about 30 weight percent acetic acid.

Another method of recovering acetic acid from an aqueous stream involves evaporating the acetic acid and water and then condensing the vapours thus formed, followed by extracting the acetic acid from the condensate by liquid-liquid extraction. Such processes are disclosed by U.S. Pat.

No. 4,401,514 (Kanzler et al.) and U.S. Pat. No. 4,102,705 (Pfeiffer et al.). However, condensation and cooling of the vapour requires additional equipment and a large amount of energy, which increases the complexity and cost of the process.

The recovery of acetate salts using evaporation has been disclosed. This involves evaporating acetic acid from solution and contacting the vapourized acetic acid produced in the evaporator with alkali, thereby producing an acetate salt. For example, U.S. Pat. No. 1,314,765 discloses recovering acetic acid from the vapours of vegetable extracts undergoing evaporation in multiple evaporation units. The process involves intimately contacting alkali, such as lime, in the form of a spray, with vapours passing from one unit to another, thereby producing the acetate salt.

U.S. Pat. No. 114,517 discloses a process whereby acetate salt of lime is recovered from acetic acid vapours by contacting the vapours with lime that is placed on trays in a cylindrical vessel. Moreover, U.S. Pat. No. 1,052,446 discloses a process of making acetate of lime that involves contacting vapours containing acetic acid with a hot calcium carbonate solution.

Likewise, U.S. Pat. No. 4,898,644 (Van Horn) discloses a process for recovering an acetate salt as a byproduct produced during the production of furfural. The process involves steam stripping organic acids, including acetic and/or formic acid from an aqueous solution containing same, and contacting the vapourized acetic acid with sodium hydroxide to form sodium acetate. Prior to removing the acetic acid, furfural may be removed from the feed stream in a furfural stripper.

However, a disadvantage of the processes of U.S. Pat. Nos. 4,898,644, 1,314,765, 114,517 and 1,052,446 is that a further step of acidification would be necessary to further purify and recover acetic acid from the solution containing the sodium acetate or calcium acetate. Prior to extraction with a solvent, acidification is necessary so that sodium acetate or calcium acetate is in the non-dissociated form, (i.e., so that it is present predominantly as the acetic acid species, rather than the acetate salt species) and this is typically carried out by using sulfuric acid, which is costly and creates sulfate salts that must be processed. Furthermore, this purification step necessitates a separate liquid-liquid extraction to recover the acetic acid. The increased chemical usage by the acidification and the requirements for additional equipment increase the cost and complexity of the process, which in turn has a negative impact on the economics of the process.

As noted previously, it is known to recover acetic acid as a byproduct during the production of furfural. Furfural is produced from the decomposition of xylose that results from the hydrolysis of the hemicellulose component of lignocellulosic feedstocks, such as wood chips. During such production processes, the raw material is fed into a reactor operating at high temperatures by the introduction of steam to produce furfural, as well as the byproducts, methanol, formic acid and acetic acid. Vapour flowing from the reactor contains water, furfural, formic acid and acetic acid and it is known to separate these acids from one another from this vapour stream and subsequently purify them.

For example, U.S. Pat. No. 4,088,660 (Puurunen) discloses such a process for producing furfural and recovering acetic acid as a byproduct. According to this process, the vapour stream produced from the reactor, containing the furfural, methanol, acetic acid and formic acid, is contacted with furfural in a gas washer and, subsequently, in an absorption tower. The furfural, which is recycled from the process, serves to absorb the acetic acid and part of the water from the vapour, thus producing an aqueous solution containing the organic acids and furfural. This aqueous solution is then dehydrated and subjected to distillation in order to separate the volatile organic acids from the furfural.

However, a drawback of the above process of Puurunen (supra) is that the solubility of furfural in water is 8.3% (83 g/L) and the solubility of water in furfural is about 5%, depending on the temperature. These mutual solubilities are too high for furfural to be an effective extractant of acetic acid from water. That is, the loss of furfural in the water phase and the need to remove water from the furfural phase would add significant cost to the operation. In addition, the extraction of acetic acid by furfural is very weak. The concentration of acetic acid in furfural is less than that in water in an acetic acid-furfural-water extraction system at 35° C. (E. L. Heric and R. M. Rutledge, (1960), Journal of Chemical Engineering Data 5(3): 272-274).

Zeitsch (The Chemistry and Technology of Furfural and its Many Byproducts (2000), ACS Sugar Series, Vol. 13, Elsevier, Köln, Germany, p. 111-113) discloses the use of triethylamine vapour to extract acetic acid vapour and purify it from an aqueous solution. Triethylamine has a boiling point of 89° C. However, triethylamine reacts with acetic acid to form a complex with a high boiling point (165° C.), which complex can be separated from water by distillation. The complex can then be split by reacting it with ethanol at elevated temperature in the presence of an ion exchange resin which produces ethyl acetate, from which acetic acid can be produced. However, since the process is complicated and requires many steps it is impractical for use on an industrial scale.

At present, none of the prior art addresses operating an efficient and economical process for recovering volatile carboxylic acids, such as at the low concentrations found in many industrial process streams, including streams obtained from lignocellulosic conversion processes. The development of such a recovery process remains a critical requirement for the utilization of carboxylic acids as byproducts of economic significance.

SUMMARY OF THE INVENTION

The present invention overcomes several disadvantages of the prior art by taking into account the difficulties encountered in recovering carboxylic acids from process streams.

According to a first aspect of the present invention there is provided a process for recovering volatile carboxylic acids from an aqueous stream containing same comprising the steps of:
(a) evaporating the aqueous stream to produce a vapour stream comprising vapourized carboxylic acid and water vapour, which aqueous stream is produced by a conversion process using a lignocellulosic feedstock as a substrate;
(b) contacting the vapour stream with an organic solvent so as to extract the volatile carboxylic acid present in the vapour stream, thereby producing a liquid stream comprising the organic solvent and the volatile carboxylic acid, and a water vapour stream, wherein the organic solvent has an atmospheric boiling point of at least about 150° C. and is insoluble in water; and
(c) separating the volatile carboxylic acid from the organic solvent.

According to one embodiment of the invention, the volatile carboxylic acid is separated from the organic solvent by distillation. In another embodiment of the invention, the organic solvent recovered by distillation is reused in the process.

According to another embodiment of the invention, in the step of contacting, the organic solvent comprises an aliphatic amine having at least 10 carbon atoms and an alkylphenol having 1 to 40 carbon atoms in its alkyl group. The alkylphenol may be nonylphenol or octylphenol. The aliphatic amine may be selected from the group consisting of tributylamine, tripentylamine, trihexylamine, trioctylamine, tridecylamine and mixtures thereof.

Preferably, the aqueous stream is produced by a conversion process using a lignocellulosic feedstock as a substrate. The lignocellulosic feedstock may be selected from the group consisting of corn stover, soybean stover, corn cobs, rice straw, rice hulls, switch grass, corn fiber, wheat straw, barley straw, canola straw, oat straw, oat hulls and combinations thereof.

In one embodiment of the invention, the aqueous stream that is evaporated is a fermentation broth comprising a fermentation product produced by pretreating a lignocellulosic feedstock with acid or alkali so as to produce a pretreated feedstock composition comprising fiber solids containing cellulose, hydrolyzing the cellulose to glucose and then fermenting the glucose to produce the fermentation broth comprising the fermentation product. In another embodiment of the invention, the aqueous stream that is evaporated is a still bottoms stream produced by pretreating a lignocellulosic feedstock with acid or alkali so as to produce a pretreated feedstock composition comprising fiber solids containing cellulose, hydrolyzing the cellulose to glucose, fermenting the glucose to produce a fermented solution comprising ethanol and distilling the fermented solution to produce concentrated ethanol and the still bottoms stream. Alternatively, the aqueous stream that is evaporated is a stream produced by hydrolyzing hemicellulose and cellulose present in a lignocellulosic feedstock with acid or alkali.

In yet another embodiment of the invention, the evaporating is conducted at a temperature of 40° C. to 145° C., or 60° C. to 120° C.

According to a further embodiment of the invention, the extracting is conducted at a temperature of about 60° C. to about 175° C., or about 60° C. to about 150° C., or about 60° C. to about 130° C.

Preferably, the carboxylic acid that is recovered is acetic acid.

In yet a further embodiment of the invention, in the step of contacting, water is insoluble in the organic solvent.

Preferably, the carboxylic acid that is present in the aqueous stream is fed to the evaporating step is at a concentration of less than about 5 wt %.

According to a second aspect of the invention, there is provided a process for recovering a volatile carboxylic acid from an aqueous stream containing same comprising the steps of:
(a) evaporating the aqueous stream to produce a vapour stream comprising the volatile carboxylic acid that has been vapourized and water vapour, which aqueous stream is produced by a conversion process that comprises the steps of pretreating a lignocellulosic feedstock with acid or alkali to produce a pretreated feedstock composition comprising fiber solids containing cellulose, hydrolyzing the cellulose to glucose with cellulase enzymes and β-glucosidase and fermenting the glucose to ethanol or butanol;
(b) contacting the vapour stream with an organic solvent so as to extract the volatile carboxylic acid present in the vapour stream, thereby producing a liquid stream comprising the organic solvent and the volatile carboxylic acid, and a water vapour stream, wherein the organic solvent has an atmospheric boiling point of at least about 150° C. and is insoluble in water; and
(c) separating the volatile carboxylic acid from the organic solvent.

According to a third aspect of the present invention, there is provided a process for recovering a volatile carboxylic acid from an aqueous stream containing same comprising the steps of:
(a) evaporating the aqueous stream to produce a vapour stream comprising the volatile carboxylic acid that has been vapourized and water vapour, which aqueous stream is produced by a conversion process that comprises the steps of pretreating a lignocellulosic feedstock with acid to produce a pretreated feedstock composition comprising fiber solids containing cellulose, hydrolyzing the cellulose to glucose with cellulase enzymes and β-glucosidase and fermenting the glucose to ethanol or butanol;
(b) contacting the vapour stream with an organic solvent so as to extract the volatile carboxylic acid present in the vapour stream, thereby producing a liquid stream comprising the organic solvent and the volatile carboxylic acid, and a water vapour stream, wherein the organic solvent has an atmospheric boiling point of at least about 150° C. and is insoluble in water; and
(c) separating the volatile carboxylic acid from the organic solvent.

The foregoing process provides a simplified and cost-effective means to recover carboxylic acids. Advantageously, the process of the invention does not require a subsequent acidification step to recover carboxylic acids, including, but not limited to acetic acid. This is in contrast to prior art methods in which acetic acid vapour is contacted with alkali to produce a solution containing an acetate salt that must be acidified to the non-dissociated form prior to recovery by liquid-liquid extraction. Thus, the present invention avoids the disadvantages inherent in such processes including the high cost of the acidification, the requirement for a separate extraction operation and the production of sulfate salts that must be further processed.

Furthermore, by contacting the carboxylic acid vapours with the organic solvent, rather than evaporating the vapour stream containing the carboxylic acid and then condensing and extracting the acid from the condensate, the use of additional equipment for condensing is avoided, as well as the high energy costs associated with such a step.

The process of the invention also overcomes the disadvantages inherent with the use of furfural to extract acetic acid, namely that furfural has a significant solubility in water. The dissolution of furfural in water is a significant cost in the process and limits the use of the water stream in the plant.

Moreover, the recovery process of the invention can be applied to a wide range of industrial process streams containing carboxylic acids, including those containing lignin and high molecular weight compounds. By contrast, liquid-liquid extraction processes are ineffective when used to recover carboxylic acids directly from streams containing these components as they can accumulate in the solvent and render it less effective.

BRIEF DESCRIPTION OF THE DRAWINGS

These and other features of the invention will become more apparent from the following description in which reference is made to the appended drawings wherein.

DETAILED DESCRIPTION OF THE INVENTION

Figure 1:
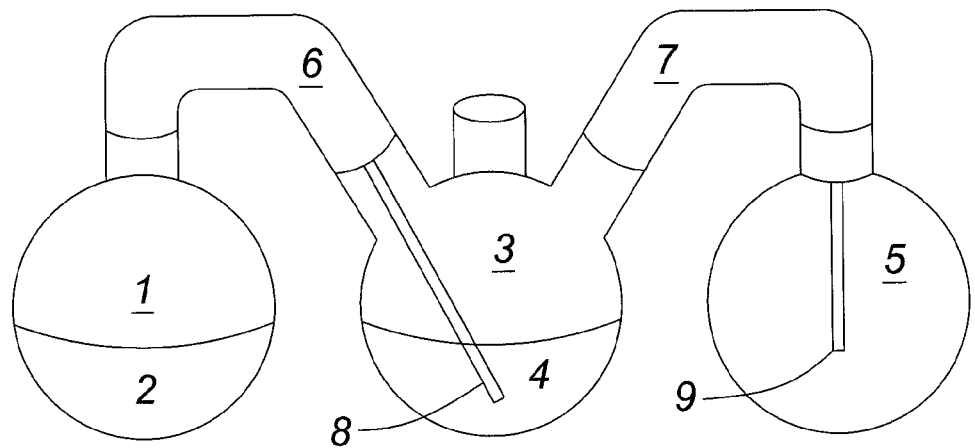
FIGS. 1 and 2 depict apparatus for recovering acetic acid from a vapour stream including a feed flask, a scrubber flask and a collection flask.

The following description is of preferred embodiments.

Carboxylic acids are organic acids characterized by the presence of at least one carboxyl group, denoted —COOH. Carboxylic acids may have more than one carboxyl group, but the presence of one carboxyl group is preferred. The simplest and preferred carboxylic groups for use in the present invention are the alkanoic acids, which are carboxylic acids of the form R—COOH. Examples of these are acetic acid, formic acid, and propionic acid. Furthermore, one or more carboxylic acids may be recovered in accordance with the invention.

The carboxylic acid recovered in accordance with the invention is a "volatile carboxylic acid". As used herein, the term "volatile carboxylic acid" refers to a carboxylic acid that has a boiling point at atmospheric pressure of less than 150° C. Compounds with a higher boiling point will not easily evaporate with water if utilized in the practice of the invention. Two examples of compounds that are volatile carboxylic acids are acetic acid (boiling point 118° C.) and formic acid (boiling point 101° C.). The boiling point of the volatile carboxylic acid is preferably at least about 80° C. at atmospheric pressure. Compounds with a boiling point lower than this can be evaporated out of water without the need of extraction. More preferably, the boiling point of the volatile carboxylic acid is at least about 100° C.

Accordingly, in one embodiment of the invention, the volatile carboxylic acid has a boiling point measured at atmospheric pressure between 80° C. and 150° C., more preferably between 100° C. and 150° C. For example, the boiling point at atmospheric pressure may be 80, 85, 90, 95, 100, 105, 110, 115, 120, 125, 130, 135, 140, 145 or 150° C.

In principal, the process of the invention can be used to recover volatile carboxylic acids from any aqueous stream containing a carboxylic(s) acids derived from an industrial process, regardless of its concentration. However, the process of the invention is particularly advantageous when recovering one or more volatile carboxylic acids from a process stream that contains less than 50 g/L (5%) volatile carboxylic acids.

Thus, in embodiments of the invention, volatile carboxylic acids are present in the aqueous stream at a concentration of between about 0.1 and about 50 g/L, about 0.5 and about 20 g/L or about 1.0 and about 15 g/L. For example, the acetic acid may be present in the sugar stream at a concentration of about 0.1, 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5 or 20.0 g/L.

Acetic acid has a $pK_a$ of about 4.75 ($K_a$ of $1.78 \times 10^{-5}$) so that at pH 4.0, about 14.8 mole % of the acid is present as acetate. Accordingly, the species present in the aqueous stream will depend on the pH of the solution. The evaporation of acetic acid is typically conducted at a pH at which acetic acid is the dominant species in solution, such as pH<pKa, although the aqueous stream may contain some acetate species. Similarly, formic acid has a pKa of 3.75 and is typically evaporated at a pH below this value.

Although the process of the invention is not constrained by the origin of the aqueous stream comprising volatile carboxylic acids, preferably such stream is derived from a process that uses a lignocellulosic material as a feedstock. According to this embodiment, the acetic acid arises from acetyl groups attached to xylan and to some extent lignin. Acetic acid possibly also arises from other constituents that are liberated as acetic acid and/or acetate by exposure to acid, alkali or other treatments of the feedstock.

Formic acid is a degradation product of sugar produced during pretreatment. Glucose is unstable in hot acid solutions and can lose three molecules of water to yield 5-hydroxymethylfurfural (HMF). HMF in turn is unstable and can add two molecules of water to yield formic acid and levulinic acid.

Representative lignocellulosic feedstocks for use in the practice of the invention are (1) agricultural wastes such as corn stover, corn cobs, wheat straw, barley straw, oat straw, rice straw, canola straw, and soybean stover; (2) grasses such as switch grass, miscanthus, cord grass, and reed canary grass; and (3) forestry wastes such as aspen wood and sawdust. These feedstocks contain high concentrations of cellulose and hemicellulose that are the source of the sugar in the aqueous stream.

Lignocellulosic feedstocks comprise cellulose in an amount greater than about 20%, more preferably greater than about 30%, more preferably greater than about 40% (w/w). For example, the lignocellulosic material may comprise from about 20% to about 50% (w/w) cellulose, or any amount therebetween. Furthermore, the lignocellulosic feedstock comprises lignin in an amount greater than about 10%, more typically in an amount greater than about 15% (w/w). The lignocellulosic feedstock may also comprise small amounts of sucrose, fructose and starch.

The aqueous stream preferably arises from a lignocellulosic conversion process in which a lignocellulosic feedstock is subjected to chemical and/or biological treatment to hydrolyze polysaccharides to produce fermentable sugar, followed by fermentation to produce a fermentation product and optionally a distillation to concentrate the fermentation product. However, streams from pulp processing and furfural production are also encompassed by the present invention as these processes produce streams containing acetic acid and formic acid at low concentrations.

According to one embodiment of the invention, the aqueous stream from which the volatile carboxylic acid is recovered is a stream resulting from pretreating the feedstock with acid, e.g., a hemicellulose hydrolysate. The acid pretreatment is intended to deliver a sufficient combination of mechanical and chemical action so as to disrupt the fiber structure of the lignocellulosic feedstock and increase the surface area of the feedstock to make it accessible or susceptible to cellulase enzymes. Preferably, the acid pretreatment is performed so that nearly complete hydrolysis of the hemicellulose and only a small amount of conversion of cellulose to glucose occurs. The majority of the cellulose is hydrolyzed to glucose in a subsequent step that uses cellulase enzymes, although a small amount of the cellulose can be hydrolyzed in this step as well. Typically a dilute acid, at a concentration from about 0.02% (w/w) to about 5% (w/w), or any amount therebetween, (measured as the percentage weight of pure acid in the total weight of dry feedstock plus aqueous solution) is used for the pretreatment.

Examples of acids that can be used in the pretreatment process include those selected from the group consisting of sulfuric acid, sulfurous acid, sulfur dioxide and a combination thereof. Preferably, the acid is sulfuric acid.

A preferred pretreatment, without intending to be limiting, is steam explosion described in U.S. Pat. No. 4,416,648 (Foody; which is incorporated herein by reference).

The acid pretreatment is preferably carried out at a maximum temperature of about 160° C. to about 280° C. The time that the feedstock is held at this temperature may be about 6 seconds to about 600 seconds. In one embodiment of the invention, the pH of the pretreatment is about 0.4 to about 3.0, or any pH range therebetween. For example, the pH of the pretreatment may be 0.4, 1.0, 1.5, 2.0, 2.5 or 3.0. Preferably, the pretreatment is carried out to minimize the degradation of xylose and the production of furfural.

In another embodiment of the invention, the chemical used for pretreatment of the lignocellulosic feedstock is alkali. The alkali used in the pretreatment reacts with acidic groups present on the hemicellulose to open up the surface of the substrate. With alkali pretreatment, acetate is produced from acetyl groups present on the hemicellulose and/or other components of the feedstock, although the amount of acetate present will vary depending on the severity of the treatment. In contrast to acid pretreatment, alkali pretreatment methods may or may not hydrolyze xylan to produce xylose.

Examples of alkali that may be used in the pretreatment include ammonia, ammonium hydroxide, potassium hydroxide, and sodium hydroxide. The pretreatment may also be conducted with alkali that is insoluble in water, such as lime and magnesium hydroxide, although the soluble bases are preferred.

An example of a suitable alkali pretreatment, that is variously called the Ammonia Freeze Explosion, Ammonia Fiber Explosion or Ammonia Fiber Expansion ("AFEX" process), involves contacting the lignocellulosic feedstock with ammonia or ammonium hydroxide in a pressure vessel for a sufficient time to enable the ammonia or ammonium hydroxide to alter the crystal structure of the cellulose fibers. The pressure is then rapidly reduced, which allows the ammonia to flash or boil and explode the cellulose fiber structure. (See U.S. Pat. Nos. 5,171,592, 5,037,663, 4,600,590, 6,106,888, 4,356,196, 5,939,544, 6,176,176, 5,037,663 and 5,171,592, which are each incorporated herein by reference). The flashed ammonia may then be recovered according to known processes.

The pretreatment produces a pretreated feedstock composition (e.g., pretreated feedstock slurry) that contains a soluble component including the sugars resulting from hydrolysis of the hemicellulose, acetic acid and other organic acids, such as galacturonic acid, formic acid, lactic acid and glucuronic acid and fiber solids including cellulose and lignin.

According to another embodiment of the invention, the soluble component of the pretreated feedstock composition is separated from the solids. This soluble fraction, which includes the sugars released during pretreatment, the acetic acid, formic acid, other organic acids and soluble components may be the aqueous stream fed to the evaporation.

The foregoing separation may be carried out by washing the pretreated feedstock composition with an aqueous solution to produce a wash stream, and a solids stream comprising the unhydrolyzed, pretreated feedstock. Alternatively, the soluble component is separated from the solids by subjecting the pretreated feedstock composition to a solids-liquid separation, using known methods such as centrifugation, microfiltration, plate and frame filtration, cross-flow filtration, pressure filtration, vacuum filtration and the like. Optionally, a washing step may be incorporated into the solids-liquids separation.

The separated solids, which contain cellulose, may then be hydrolyzed to glucose. The hydrolysis may be conducted with cellulase enzymes, which are discussed in more detail hereinafter. The resulting glucose-containing stream may then be the aqueous stream fed to the evaporator.

According to yet another embodiment of the invention, the soluble component of the pretreated feedstock composition is not separated from the fiber solids. In this embodiment, the entire pretreated feedstock composition, which will include any sugars resulting from hemicellulose hydrolysis, is subjected to cellulose hydrolysis. This produces a sugar stream that may be the aqueous stream sent to the evaporating step for recovery of volatile carboxylic acids. Preferably, the cellulose hydrolysis is conducted with cellulase enzymes. A major component of this sugar stream will be glucose, although pentose sugars derived from the hemicellulose component will be present as well.

Prior to hydrolysis with cellulase enzymes, the pH of the pretreated feedstock composition is adjusted to a value that is amenable to the cellulase enzymes, which is typically between about 4 and about 6, although the pH can be higher if alkalophilic cellulases are used. The temperature of the hydrolysis is 40° C. to 65° C. unless thermophilic cellulases are used so that higher temperatures can be utilized.

The enzymatic hydrolysis can be carried out with any type of cellulase enzymes capable of hydrolyzing the cellulose to glucose, regardless of their source. Among the most widely studied, characterized and commercially produced cellulases are those obtained from fungi of the genera *Aspergillus*, *Humicola*, and *Trichoderma*, and from the bacteria of the genera *Bacillus* and *Thermobifida*. Cellulase produced by the filamentous fungi *Trichoderma longibrachiatum* comprises at least two cellobiohydrolase enzymes termed CBHI and CBHII and at least four EG enzymes. As well, EGI, EGII, EGIII, EGV and EGVI cellulases have been isolated from *Humicola insolens* (see Schulein et al., *Proceedings of the Second TRICEL Symposium on Trichoderma reesei Cellulases and Other Hydrolases*, Espoo 1993, P. Suominen and T. Reinikainen, Eds. Foundation for Biotechnical and Industrial Fermentation Research, Helsinki 8:109-116, which is incorporated herein by reference).

The enzymatic hydrolysis is carried out in batch, fed batch, or continuous systems. The hydrolysis system may be mixed or unmixed, or mixed part of the time or only in some regions or reactors. The hydrolysis may be carried out as a single stage operation or a multistage operation. The solids consistency during hydrolysis may be 5% to 25% on a weight basis. The cellulase enzyme dosage may be 3 to 50 mg cellulase per gram cellulose. The hydrolysis is run for a time period of 3 to 200 hr. The volume of a hydrolysis vessel is 100,000 to 4 million liters.

Following cellulose hydrolysis of the pretreated feedstock slurry, any insoluble solids, including, but not limited to lignin, present in the resulting sugar stream may be removed using conventional solid-liquid separation techniques prior to any further processing. These solids may be burned to provide energy for the entire process. However, it should be appreciated that lignin may be removed at other stages of the process.

The sugar stream may then be fermented by microbes to produce a fermentation broth comprising a fermentation product. As used herein and as would be familiar to those of skill the art, the terms "fermentation broth" and "fermentation stream" are interchangeable. According to one embodiment of the invention, the fermentation broth is the aqueous stream sent to the evaporation for carboxylic acid recovery.

For ethanol production, the fermentation may be carried out with a *Saccharomyces* spp. yeast. Preferably, glucose and any other hexoses typically present in the sugar stream are fermented to ethanol by wild-type *Saccharomyces cerevisiae*, although genetically modified yeasts may be employed as well. For example, if pentose and hexose sugars are present, the fermentation may be performed with a recombinant *Saccharomyces* yeast that is engineered to ferment both hexose and pentose sugars to ethanol. Recombinant yeasts that can ferment the pentose sugar, xylose, to ethanol are described in U.S. Pat. No. 5,789,210, the contents of which are herein incorporated by reference. Furthermore, the pentose sugars, arabinose and xylose, may be converted to ethanol by the yeasts described in Boles et al. (WO 2006/096130, which is incorporated herein by reference).

It is understood by those skilled in the art that the fermentation microbes can produce and/or consume acetic acid. The concentration of acetic acid fed to the fermentation is therefore not necessarily equal to that in the product of the fermentation.

Examples of other fermentation products included within the scope of the invention include sorbitol, butanol, 1,3-propanediol and 2,3-butanediol. Other microorganisms that may be employed in the fermentation include wild-type or recombinant *Escherichia, Zymomonas, Candida, Pichia, Streptomyces, Bacillus, Lactobacillus* and *Clostridium*.

In practice, the fermentation is performed at or near the temperature and pH optima of the fermentation microorganism. A typical temperature range for the fermentation of glucose to ethanol using *Saccharomyces cerevisiae* is between about 25° C. and about 35° C., although the temperature may be higher if the yeast is naturally or genetically modified to be thermostable. The pH of a typical fermentation employing *Saccharomyces cerevisiae* is between about 3 and about 6. The dose of the fermentation microorganism will depend on other factors, such as the activity of the fermentation microorganism, the desired fermentation time, the volume of the reactor and other parameters. It should be appreciated that these parameters may be adjusted as desired by one of skill in the art to achieve optimal fermentation conditions.

The sugar stream may also be supplemented with additional nutrients required for the growth of the fermentation microorganism. For example, yeast extract, specific amino acids, phosphate, nitrogen sources, salts, trace elements and vitamins may be added to the hydrolyzate slurry to support their growth.

The fermentation may be conducted in batch, continuous or fed-batch modes with or without agitation. Preferably, the fermentation reactors are agitated lightly with mechanical agitation. A typical, commercial-scale fermentation may be conducted using a series of reactors, such as 1 to 6. The fermentation microorganisms may be recycled back to the fermentor or may be sent to distillation without recycle.

It should be understood that the hydrolysis and fermentation reactions can be conducted simultaneously in the same reactor, although it is preferred that the hydrolysis and fermentation are performed separately to achieve the optimal temperature for each process.

The fermentation broth that is sent to distillation is a dilute alcohol solution containing solids, including unconverted cellulose, and any components added during the fermentation to support growth of the microorganisms. Microorganisms are potentially present depending upon whether or not they are recycled during the fermentation. The broth is preferably degassed to remove carbon dioxide and then pumped through one or more distillation columns to separate the alcohol from the other components in the broth. The mode of operation of the distillation system depends on whether the alcohol has a lower or a higher boiling point than water. Most often, the alcohol has a higher boiling point than water, as is the case when ethanol is distilled.

In embodiments wherein ethanol is concentrated, the column(s) in the distillation unit is preferably operated in a continuous mode, although it should be understood that batch processes are also encompassed by the present invention. Heat for the distillation process may be introduced at one or more points either by direct steam injection or indirectly via heat exchangers. The distillation unit may contain one or more separate beer and rectifying columns. In this case, dilute beer is sent to the beer column where it is partially concentrated. From the beer column, the vapour goes to a rectification column for further purification. Alternatively, a distillation column is employed that comprises an integral enriching or rectification section. After distillation, the water remaining may be removed from the vapour by a molecular sieve resin, by adsorption, or other azeotrope-breaking methods familiar to those of skill in the art. The vapour may then be condensed and denatured.

An aqueous stream(s) remaining after ethanol distillation and containing solids, referred to herein as "still bottoms", is withdrawn from the bottom of one or more of the column(s) of the distillation unit. The volatile carboxylic acid(s) in this still bottoms stream may then be recovered by the evaporation process of the present invention. This stream will contain the volatile carboxylic acid, inorganic salts, unfermented sugars and organic salts.

When the alcohol has a higher boiling point than water, such as butanol, the distillation is run to remove the water and other volatile compounds from the alcohol. The water vapor exits the top of the distillation column and is known as the "overhead stream". The overhead stream can contain volatile carboxylic acids and is condensed prior to recovery of the carboxylic acid by the evaporation process described herein.

As used herein, the term "evaporating" refers to those processes that utilize one or more evaporators to produce a vapour stream comprising the volatile carboxylic acid and water. The term "evaporating" excludes producing vapour streams containing the volatile carboxylic acid by distillation or by steam stripping, although these processes may be carried out prior to or after the evaporating step of the present invention.

According to the process of the invention, evaporation is effected so as to vapourize both water and the volatile carboxylic acids contained in the aqueous stream. The vapour stream produced from the evaporation is contacted with an organic solvent which serves to extract the volatile carboxylic acid. In one embodiment of the invention, the evaporation is carried out to achieve the maximum practical concentration of solids in the aqueous stream, although the practice of the invention is not constrained by the solids concentration achieved. Such maximum solids concentration depends on the viscosity of the stream, the formation and management of solid precipitates, and the type of evaporator used. The maximum solids concentration for natural circulation or falling-film evaporators is typically 30% to 55% by weight. More typically, it is 37% to 41% by weight. However, with forced recirculation, a solids concentration of as high as 70% to 80% can be reached.

The evaporation may be conducted by processing the aqueous stream comprising the volatile carboxylic acid(s) with any suitable evaporator known to those of skill in the art. This includes natural/forced circulation evaporators, falling film evaporators, rising film evaporators, plate evaporators, thin film evaporators, mechanical vapor recompression evaporators, thermal vapor recompression evaporators, evaporator/crystallizers, or combinations thereof. Evaporators used in industry contain a heating section, a concentrating and separating section and a vacuum or pump to provide pressure. The most common heating section used in industry consists of parallel tubes, although plates and coils may be used as well. However, evaporators for use in the present invention do not condense a significant amount of vapours arising from the concentration and separating section.

Natural circulation evaporators rely on the natural circulation caused by density differences that arise from heating in evaporators using heating tubes as the source of heat. In this regard, as the water begins to boil, bubbles will rise and cause circulation, which facilitates the separation of the liquid and the vapour at the top of the heating tubes. Forced circulation evaporators employ a pump to increase pressure and circulation. This can avoid drying out of the system that can occur when using such evaporators.

Falling film evaporators are particularly suitable for viscous solutions. Such evaporators are generally made of bundles of long tubes that are surrounded by a steam jacket. Liquid flows downward in each tube, forming a thin film on the inside wall, while steam condenses and flows downward on the outer surface of the tube. Boiling/evaporation take place in the thin film because of the heat applied by the steam. The vapour produced by this boiling/evaporation and the liquid concentrated by the process flow downward. The vapour leaves the top of the evaporator, while the concentrated liquid is discharged from the bottom of the unit.

Rising film evaporators operate on a "thermo-siphon" principle. The feed enters the bottom of the heating tubes and, as it heats, steam begins to form. This ascensionial flow of steam causes liquid and vapours to flow upwards co-currently, which has the beneficial effect of increasing the degree of turbulence in the liquid.

Plate evaporators are also included within the scope of the invention. Such evaporators use framed plates, having passages for vapour flow, as a heating means instead of tubes. During evaporation, steam alternatively ascends and descends parallel to the concentrated liquid, thus following a co-current, counter-current path in relation to the liquid. These evaporators typically do not exceed 3-4 m in height and thus find use in applications where space is limited.

Thin film evaporators have a surface over which the incoming aqueous stream flows downward. A mechanical blade moves across the liquid film to keep the liquid flowing and move solid particles. Thin film evaporators are particularly useful for extremely viscous streams.

Mechanical vapor recompression (MVR) systems are equipped with one or more compressors to increase the pressure of the vapor stream. This increases the condensation temperature of the vapor. With the vapor at a higher temperature, it can then be used to provide energy to the system.

Thermal vapor recompression (TVR) systems are equipped with one or more steam jet ejectors. The steam is passed through these to increase its pressure and thereby decrease steam usage in the process.

Evaporator/crystallizers are used typically in the final stage of evaporation, to produce the purified solids product. The feed to these systems is usually pre-concentrated by using one or more of the previously described operations. In the evaporator/crystallizer, the concentration of the aqueous stream is increased by evaporation, to the point where the solids precipitate as the desired crystals.

Alternately, flashing or flash evaporation can be carried out. According to this process, the incoming aqueous stream is pressurized and heated, and then fed through a throttling valve into a flash drum. Because of the large pressure drop, part of the fluid vaporizes rapidly. The result is a vapour stream that is richer in the more volatile component than the remaining liquid. Advantageously, because of the reduced pressure, the flash evaporators require less heat (and then less fuel) than other evaporation methods. However, multiple flashes are required to achieve a high level of removal of volatile compounds.

The evaporation may be carried out in a single-stage evaporator or may be part of a multiple-effect system, i.e., a system in which more than one evaporator is employed. Multiple-effect evaporator systems are preferred as they can reduce heating requirements and the resultant energy usage. A total of 4 to 7 effects are preferred to achieve the optimum steam economy. A multiple-effect evaporator system utilized in accordance with the invention can be forward fed, meaning that the feeding takes place so that the solution to be concentrated enters the system through the first effect, which is at the highest temperature. Partial concentration occurs in the first effect, with vapour sent to the second effect to provide heat for same. The partially concentrated solution is then sent to the second effect where it is again partially concentrated, with vapour sent to the third effect, and so on. Alternatively, backward feeding may be utilized, in which the partially concentrated solution is fed from effect to effect with increasing temperature. In either case, vapor streams traversing from one effect to another would be sent to an extractor to remove the volatile carboxylic acid.

A person of skill in the art can readily choose a suitable operating temperature. This may involve taking into account the design considerations set forth below. In embodiments of the invention, the evaporator operating temperature can be between about 40° C. and about 145° C. In another embodiment of the invention, the temperature is between about 60° C. and about 120° C. It will be understood that the temperature is measured under the operating pressure, which is typically under vacuum or at atmospheric pressure, but can be at higher pressure. Furthermore, for the purposes of this specification, when using multiple-effect evaporators, the temperature of the evaporation is considered to fall within the 40-145° C. temperature range if the temperature measured in each effect, and at any location within any given effect, falls within said range.

Dilute acetic acid in water has an atmospheric boiling point slightly above 100° C., which is close to that of water. When the evaporation is carried out at atmospheric pressure, the temperature is high enough to boil the aqueous stream and will therefore be somewhat higher than 100° C. The boiling point might increase with increases in solids concentration, so atmospheric evaporations at temperatures of 110° C. to 120° C. are common. The evaporation can also be carried out under vacuum, in which case the boiling point of the aqueous stream will be below 100° C. and hence the evaporator will be operated at the lower temperature. Although the invention is not constrained by the temperature of the evaporation, there is a cost associated with maintaining a strong vacuum. Thus, it may be advantageous to not operate the evaporation below about 40° C. In one embodiment, the lower temperature limit is 50° C. or, more preferably, 60° C.

Alternately the evaporation can be carried out under pressure. Evaporators operate at up to 50 psig pressure, which corresponds to boiling water at 145° C. Advantageously, the higher pressure decreases the volume of the vapour and thereby the size of the equipment. Although pressure approaching or exceeding 50 psig can be utilized in the practice of the invention, it should be appreciated that conducting the evaporation at these high pressures requires the use of pressure vessels.

While single effect evaporators operate at a single temperature, multiple effect evaporators operate at the highest temperature in the first effect, and then the temperature drops 5 to 7° C. with each additional effect. For example, the first effect could run at atmospheric pressure at about 100° C., with subsequent effects under vacuum at temperatures decreasing down to a lower limit of 40 to 60° C. Alternately, all effects might be pressurized and run at temperatures higher than 100° C., with subsequent effects at lower temperatures above 100° C. Moreover, the first effect might be under pressure at a temperature higher than 100° C. and downstream, cooler effects under vacuum at temperatures lower than 100° C.

The vapours exiting the evaporator(s) are contacted with the organic solvent. In industry, such an extraction would be carried out in an "extractor" or a series of extractors. As used herein, an "extractor" is any device that contacts the organic solvent with the vapour stream so as to extract and thereby remove the volatile carboxylic acid therefrom. The organic solvent is maintained at a temperature sufficiently high so that the water remains vapourized. The extractor then contains a mixture of the volatile carboxylic acid and the organic solvent. The volatile carboxylic acid can then be recovered from the mixture by distillation or other expedients. Preferably, the water vapour does not condense in the extractor to any significant extent, but rather escapes as steam that can optionally be used in the process.

The aqueous stream comprising volatile carboxylic acids may comprise other volatile compounds that will be present in the vapour exiting the evaporator. These compounds will either be extracted by the solvent or will be carried with the water vapour through the solvent. If extracted with the solvent, the compounds can be removed in the subsequent distillation. If carried with the water vapour, the compounds can be further processed with the water.

An example of an extractor that is suitable for use in the invention is a scrubber. Scrubbers that are used in industry employ a liquid to "wash" unwanted pollutants in a gas stream. According to the present invention, a scrubber may be utilized to contact or "wash" volatile carboxylic acid from the vapour stream with the organic solvent so as to extract it. Although either wet or dry scrubbing techniques can be employed to extract the volatile carboxylic acid from the vapour stream, wet scrubbing is preferred.

Wet scrubbing involves contacting a gas stream with a solution, also known as a "scrubbing solution". According to the present invention, the scrubbing solution employed would be the organic solvent. Removal efficiency may be improved by increasing the residence time in the scrubber or by increasing the surface area of the organic solvent by the use of a spray nozzle, packed towers or an aspirator. Steam that escapes from the top of the scrubber may optionally be reused in the process.

Dry or semi-dry scrubbing may also be utilized. In this embodiment, the media used for removal of the volatile carboxylic acid from the vapour stream could be activated alumina impregnated with the organic solvent. Alternatively, the organic solvent could be injected directly into the scrubber. Another means to contact carboxylic acid vapours with the organic solvent would be to introduce the organic solvent to the scrubber as an atomized solution.

The term "organic solvent" refers to the liquid that extracts the carboxylic acid vapour. The word "organic" in this context means that the solvent is entirely or almost entirely composed of one or more chemical compounds whose molecules contain carbon, except for simple oxides, carbonates, cyanides, and pure carbon. The organic solvent is a solvent for the volatile carboxylic acid, which means it dissolves at least 50 g/L of the volatile carboxylic acid (w/v) at ambient temperature.

Preferably, the organic solvent has a much higher affinity for the volatile carboxylic acid than water. The affinity of the solvent for the volatile carboxylic acid is quantified by the Distribution Coefficient, D. This is measured at a temperature of 30° C. or 50° C. by contacting equal volumes of organic solvent and aqueous stream containing, for example, 10 to 20 g/L of the volatile carboxylic acid and mixing gently to reach equilibrium, which may require up to about 1 hour. The concentration of the volatile carboxylic acid is then determined in the aqueous phase and the organic phase. D is the ratio of the volatile carboxylic acid concentration in the organic phase to that in the aqueous phase. Preferably, D is greater than 5. More preferably, D is greater than 50, most preferably greater than 100. If D is much lower than these values, a large amount of the organic solvent is required to extract the volatile carboxylic acid, and this adds to the cost of the process.

The volatile carboxylic acid is extracted with an organic solvent that is insoluble in water. When referring herein to the organic solvent as "insoluble in water", it is meant that it has a solubility that is less than 5% by weight in water. In embodiments of the invention the solubility may be less than 2% by weight, less than 1% by weight or less than 0.3% by weight. Most preferably, the organic solvent has zero solubility in water. For example, the solubility of the organic solvent in water may 0 or less than 2, 1.9, 1.8, 1.7, 1.6, 1.5, 1.4, 1.3, 1.2, 1.1, 1.0, 0.9, 0.8, 0.7, 0.6, 0.5, 0.4, 0.3, 0.2 or 0.1 (w/w) at 100° C.

If the solvent is soluble in water, some of the organic solvent will be lost to the water phase. This would be a significant drawback to the process as it would complicate recovery of the organic solvent for reuse in the process. That is, if solvent is present in the water phase it has to be recovered or it is lost and must be replaced with fresh solvent, which is costly. By using an organic solvent that is insoluble with water, this removal step is avoided.

Furthermore, in embodiments of the invention, water is insoluble (zero solubility) or has low solubility in the organic solvent, such as less than 10% by weight, or more preferably less than 3% by weight. Such an embodiment is advantageous as the presence of less water in the solvent phase simplifies recovery of the volatile carboxylic acid. For example, the solubility of water in the organic solvent may be 0 or less than 10, 9, 8, 7, 6, 5, 4, 3, 2, 1.9, 1.8, 1.7, 1.6, 1.5, 1.4, 1.3, 1.2, 1.1, 1.0, 0.9, 0.8, 0.7, 0.6, 0.5, 0.4, 0.3, 0.2 or 0.1% (w/w) at 100° C.

The carboxylic acid vapour must be in contact with the solvent for a sufficient time to be extracted by the solvent. In embodiments of the invention, this is one second to a few minutes.

A temperature range of 60° C.-175° C., or any temperature therebetween, can be employed in the extraction of the vapour stream, which temperature is measured under the operating pressure of the extractor, which may be under pressure, at atmospheric pressure, at a pressure higher than atmospheric, or a combination thereof. For example, the temperature may be 60, 65, 70, 75 80, 85, 90, 95, 100, 105, 110, 115, 120, 125, 130, 135, 140, 145, 150, 155, 160, 165, 170 or 175° C. A suitable operating temperature and pressure may be selected based on the design considerations set out in more detail hereinafter.

In embodiments of the invention, the extracting step is performed at a temperature that is high enough to avoid significant condensation of water. When the extracting is operated at or near atmospheric pressure, the boiling point of water in the extractor is 100° C., and the extractor is thus maintained above this temperature to avoid such condensation. It should be understood that small amounts of water can condense during the extraction and form a separate phase. However, these small quantities of water can be easily removed from the organic phase by decanting or other means.

According to another embodiment of the invention, the extracting is preferably performed at a temperature that is low enough so that significant amounts of the organic solvent are not volatilized. Since the organic solvent has an atmospheric boiling point of at least about 150° C., if the operating temperature (at atmospheric pressure) is at or less than 150° C., losses of the solvent to evaporation are reduced or prevented. In another embodiment, the temperature is well below 150° C., such as a temperature below about 130° C. However, when the extraction is performed under vacuum, the temperature can be as low as about 60° C., as discussed below.

Furthermore, there is a risk of loss of the volatile carboxylic acid from the organic solvent at temperatures well above its boiling point. Thus, in embodiments of the invention the extraction is conducted at temperatures that are not significantly above the boiling point of the volatile carboxylic acid.

In view of the foregoing, a preferred operating temperature when the volatile carboxylic acid is extracted at atmospheric pressure would be between about 100° C. and about 150° C. or between about 100° C. and about 130° C. For example, the operating temperature of the extraction at atmospheric pressure may be 100, 101, 102, 103, 104, 105, 106, 107, 108, 109, 110, 111, 112, 113, 114, 115, 116, 117, 118, 119, 120, 121, 122, 123, 124, 125, 130, 135, 140, 145, 149 or 150° C. Advantageously, these temperatures are below the boiling point of the organic solvent, at or above the boiling point of water and not significantly above the boiling point of the carboxylic acid at atmospheric pressure.

Since the boiling point of acetic acid is 118° C. at atmospheric pressure, it is preferable to operate the extraction below about 130° C. (at atmospheric pressure) when this acid is recovered to avoid significant loss of acetic acid. Thus, in those embodiments where acetic acid is recovered, the temperature of the acetic acid extraction at atmospheric pressure is preferably higher than 100° C. and below 130° C., or any temperature therebetween. For example, the temperature at atmospheric pressure may be 100° C., 101, 102, 103, 104, 105, 106, 107, 108, 109, 110, 111, 112, 113, 114, 115, 116, 117, 118, 119, 120, 121, 122, 123, 124, 125, 126, 127, 128, 129 or 130° C.

The extractor can also be run under a pressure greater than atmospheric or under a vacuum. Preferably, the extraction is run under a vacuum. However, in either case, the extractor is preferably maintained at a temperature higher than the boiling point of water at the operating pressure and a temperature below the boiling point of the organic solvent at the operating pressure. In an even more preferred embodiment, the temperature is not significantly above the boiling point of the volatile carboxylic acid at the operating pressure. A preferred operating range when a volatile carboxylic acid is extracted under vacuum is about 60° C. to about 100° C. For example, the extraction under vacuum may be conducted at a temperature of 60, 65, 70, 75, 80, 85, 90, 95 or 100° C.

The volatile carboxylic acid can be readily recovered from the solvent by evaporation or distillation if the boiling point of the solvent significantly exceeds that of the volatile carboxylic acid. For example, since acetic acid has a boiling point of 118° C. at atmospheric pressure, when this acid is recovered, the recovery of the organic solvent is most easily achieved if the boiling point of the organic solvent greatly exceeds about 118° C.

Representative examples of organic solvents that may possess the foregoing properties include aliphatic amines having at least 10 carbon atoms. An example of a suitable aliphatic amine is, but is not limited to, tributylamine, tripentylamine, trihexylamine, trioctylamine, tridecylamine or mixtures thereof. Preferred mixtures of aliphatic amines are mixtures of trioctylamine and tridecylamine in ratios of 70/30, respectively, to 30/70, respectively. A commercial product that is a mixture of aliphatic amines is Alamine® 336, which is an organic solvent commercially available from Cognis that contains a ratio of trioctylamine to tridecylamine of 2/1.

Optionally, the organic solvent includes a co-solvent such as a phenol or a naphthol to facilitate phase separation and selectivity for the volatile carboxylic acid. The phenol or naphthol may be alkylated, having 1 to 40 carbon atoms in the alkyl group. An example of a suitable phenol is nonylphenol. This compound is available commercially as p-nonylphenol from Schenectady International. Another suitable phenol is octylphenol. Non-limiting examples of suitable naphthols are 1-naphthol and 2-naphthol.

Preferably, if a phenol is utilized as a co-solvent in combination with one or more aliphatic amines, the mixture of the phenol and one or more aliphatic amines contains 40% to 80% of the phenol with the balance of the mixture being the aliphatic amine(s).

Amines that are particularly suitable for use in the invention include tridecylamine or trioctylamine that each have a solubility in water of less than 5 parts per million (ppm) and boiling points that are roughly 350° C. Nonylphenol has a solubility in water of 0.08% at 22° C. and an atmospheric boiling point of 300° C. and thus is also particularly suitable for use in the invention. However, the practice of this invention is not constrained by the use of any particular compound or compounds making up the organic solvent. That is, other organic solvents may be selected with similar or other desirable properties to those set forth above.

As set forth above, the extraction produces a mixture of the organic solvent and the volatile carboxylic acid, for example acetic acid, with reduced water content since the water vapour escapes from the extractor. The volatile carboxylic acid is then separated from the organic solvent. In one embodiment of the invention, the volatile carboxylic acid has a significantly lower boiling point than the organic solvent, thereby allowing these two components to be easily separated from one another by heating. That is, the volatile carboxylic acid can be heated to boil while the organic solvent does not. This heating can be carried out by evaporation or distillation.

In those embodiments in which acetic acid is separated from the organic solvent at atmospheric pressure, such separation is preferably at a temperature that is higher than about 118° C. and lower than the boiling point of the solvent. When acetic acid is separated from a nonylphenol and mixed triamine solvent, the separation is preferably carried out by heating to a temperature of about 180° C. to about 240° C. at atmospheric pressure. More preferably, the temperature is about 190° C. to about 210° C. at atmospheric pressure.

Without intending to be limiting, in practice, several factors can be taken into consideration to achieve optimal separation, while minimizing cost. For instance, at pressures other than atmospheric, the temperature is generally chosen so as to be above the boiling point of the volatile carboxylic acid and below that of the solvent at the operating pressure. A pressure higher than atmospheric has the advantage that the density of the vapour phase is higher, which decreases the size of the distillation or evaporation equipment. However, the higher pressure requires steam at higher pressure to heat the system, and the high pressure steam is expensive to produce. In addition, the solvent may have limited stability at the higher temperature. Operation under vacuum reduces the temperature and the steam pressure required, and can preserve the stability of the solvent. However, the lower density of the vapour phase increases the size of the equipment required. In addition, if the boiling point of the volatile carboxylic acid is well below 100° C. at the operating pressure, a source of chilled water might be required, which adds to the operating cost of the process.

If the volatile carboxylic acid is separated from the solvent by distillation, the distillation column can consist of trays or packing. Any suitable tray or packed column can be utilized in accordance with the invention, although the following factors may be taken into consideration when making an appropriate selection. For instance, a tray column may be preferred, as it is less expensive. On the other hand, a packed column, which can contain random packing or structured packing, has a lower pressure drop and a higher efficiency than a tray column. However, the packing is susceptible to fouling by particulates in the process streams or by products from degradation reactions. Packed columns also require distributors and collectors in each stage, which adds to the cost. A person of skill in the art could weigh the advantages and disadvantages of using a tray or packed column and accordingly chose one appropriate for the separation at hand.

After separation by heating or distillation, the volatile carboxylic acid vapour is condensed to produce a concentrated stream of the volatile carboxylic acid. If the volatile carboxylic acid is produced by distillation, the condenser can be at the top of the distillation column or can be located at or near the ground. The carboxylic acid vapour can be condensed in the presence of water, if desired. In one advantageous embodiment of the invention, the amount of water present is low enough so that it does not dilute the acid to such an extent that it makes the water expensive to remove. A preferred amount of water present is 0% to 50% of the weight of acid. After removal of the volatile carboxylic acid from the organic solvent, the organic solvent can be reused in the extractor. If there are contaminants present in the carboxylic acid, a second distillation can be run to further purify the product.

The present invention will be further illustrated in the following examples. However, it is to be understood that these examples are for illustrative purposes only, and should not be used to limit the scope of the present invention in any manner.

EXAMPLES

Example 1

Extraction of Acetic Acid from the Vapour Phase at Atmospheric Pressure Using the Apparatus of FIG. 1

This example demonstrates, using the lab scale apparatus shown in FIG. 1, that a solution of acetic acid can be effectively recovered from an acetic acid-containing vapour stream by contacting the vapour stream with an organic solvent. In this particular example, the organic solvent employed was a mixture of the aliphatic amine, Alamine® and the alkylphenol, nonylphenol.

The apparatus shown in FIG. 1 depicts a feed flask 1, a scrubber flask 3 and a collection flask 5. A first glass adaptor 6 connects the feed flask 1 to the scrubber flask 3 and a second glass adaptor 7 connects the scrubber flask 3 to the collection flask 5. Both glass adaptors 6 and 7 are insulated using glass wool and wrapped in aluminum foil. Inserted into the end of glass adaptor 6 that is connected to scrubber flask 3 is a glass inlet tube 8, which, in turn, extends into scrubber flask 3. A similar glass inlet tube 9 is inserted into the end of glass adaptor 7 connected to collection flask 5 and extends into collection flask 5.

The recovery of acetic acid was carried out as follows. Feed flask 1, containing 50 mL of an aqueous 3.4% (34.14 g/L) acetic acid solution 2, and the scrubber flask 3 containing 50 mL of scrubbing solution, i.e., organic solvent 4, which was a 30:70 mixture of Alamine® 336 and nonylphenol, were heated in a 140° C. oil bath (not shown). Simultaneously, the collection flask 5 was cooled to 0° C. in an ice-water bath. With heating, the vapour generated in the feed flask 1 (the feed reflux temperature is 101° C.) was directed through the gas inlet tube 8 into the scrubbing solution (i.e., organic solvent 4) and bubbled through it. The glass adaptor 7 connecting the scrubber flask 3 to the collection flask 7 directs the vapour generated, after passing through the organic solvent 4, to gas inlet tube 9 and then into the cooled collection flask 5 where it condenses. After 75 minutes, 24 mL of an aqueous solution was recovered in the collection flask 5 and 19 mL of liquid remained in the feed flask 1. The recovered aqueous solution in the collection flask 5 contained 1.76 g/L of acetic acid. The organic solvent removed 0.78 g of acetic acid from the 24 mL recovered in the collection flask 5 or 94.8% of the acetic acid.

Example 2

Figure 2:
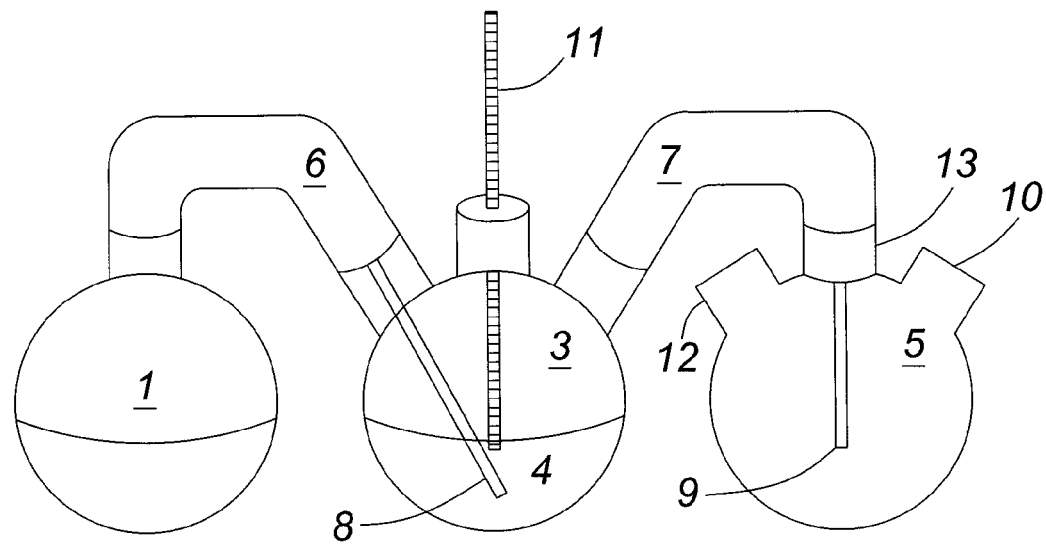

Extraction of Acetic Acid from the Vapour Phase at Atmospheric Pressure Using the Apparatus of FIG. 2

The experiment set forth in this example is similar to that described in Example 1 in that a solution containing acetic acid was passed through a scrubber flask and the acid was extracted by an organic solvent composed of a mixture of Alamine® 336 and nonylphenol during the vapour phase extraction. However, in this case the temperature of the scrubber flask was monitored and found to be 114-122° C. Furthermore, after the steam extraction, the lower limit of the apparent Distribution Coefficient (DA) was determined to be about 11 where DA=[Acetic acid]organic phase/[Acetic acid]aqueous phase.

The lab scale apparatus utilized in this example is shown in FIG. 2 and is similar to the apparatus in FIG. 1 but differs in the design of the collection flask 5 and the use of a temperature adaptor and thermometer 11 in scrubber flask 3. In FIG. 2, the collection flask 5 is a three neck flask having a first outwardly extending neck 12, a central neck 13 and a second outwardly extending neck 10, with the central neck 13 connected to the end of the glass adaptor 7. The second outwardly extending neck 10 of collection flask 5 is open to the atmosphere and the first outwardly extending neck 13 is closed using a rubber septa (not shown).

The recovery of acetic acid was carried out as follows. The scrubber flask 3 containing 50 mL of scrubbing solution, i.e., organic solvent 4, which was a 30:70 mixture of Alamine® 336 and nonylphenol, was heated in a 135-140° C. oil bath (not shown) until the internal temperature of the scrubber flask 3 reached 125° C. Simultaneously, the collection flask 5 was cooled to 0° C. in an ice-water bath. When the organic solvent 4 reached the target temperature, the feed flask 1, containing 49 mL of an aqueous 2.8% (28.34 g/L, 1.39 g of acetic acid) acetic acid solution 2, was then connected to scrubber flask 3 and heated using a 140° C. heating mantle. With heating, and after about 5 minutes, the vapour generated in the feed flask 1 (the feed reflux temperature was 101° C.) was directed through the gas inlet tube 8 into the organic solvent 4 and bubbled through it. Within 5-10 minutes the internal temperature in the scrubber flask 3 dropped to 114° C. and then drifted up to 122° C. as the oil temperature was raised to 160° C. The glass adaptor 7 connecting the scrubber flask 3 to the collection flask 7 directs the vapour generated, after passing through the organic solvent 4, to gas inlet tube 9 and then into the cooled collection flask 5 where it condenses. After 50 minutes, 31.5 mL (containing 0.06 g acetic acid) of an aqueous solution was recovered in the collection flask 5 and 8.5 mL of liquid (61.36 g/L, 0.52 g acetic acid) remained in the feed flask 1. The apparatus was removed from the heating and cooling sources. A small amount of aqueous solution (3.5 mL) collected in the bottom of scrubber flask 3 and was removed. The recovered aqueous solution in the collection flask 5 contained 1.94 g/L (0.06 g) of acetic acid.

A 5 mL aliquot of the organic solvent, now containing acetic acid, was extracted with an equal volume of a 71.5 g/L NaOH solution to directly determine the amount of acetic acid bound to the organic solvent. The organic solvent in scrubber flask 3 was found to contain 21.54 g/L (0.68 g of acetic acid) or at least 78.25% of the acetic acid removed from the feed flask. The apparent Distribution Coefficient (DA) was at least 21.54/1.94=11.1. It should be noted that DA differs from the D described above in that DA is the ratio of the concentration of acetic acid in two different vessels. Furthermore, moisture that accumulates through the glass adaptors 6 was not accounted for in this example. With time, the feed acetic acid concentration becomes more concentrated and the vapour in the glass adaptor 6 also becomes richer in acetic acid. In a large scale process this acetic acid would be captured by the organic solvent.

Example 3

Liquid-liquid Extraction of Acetic Acid with Alamine® 336 and Nonylphenol at Atmospheric Pressure This example demonstrates that acetic acid can be extracted via liquid-liquid extraction using Alamine® 336 and nonylphenol at high temperatures typical of a vapour phase extraction. In addition, it was found that increasing amounts of acetic acid were extracted as the feed acetic acid concentration was increased.

The liquid-liquid extraction of acetic acid was carried out as follows. A volume ratio of 1:1 organic to aqueous phase was used with a total volume of 10 mL. The organic phase was a mixture of Alamine® 336 to nonylphenol at a ratio of 30:70 by weight and the aqueous solutions used are listed in Table 1. Alamine® 336 is a 2:1 ratio of trioctylamine to tridecylamine. The extractions were conducted in 25 mL Erlenmeyer flasks in an incubator shaker, 400 r.p.m. at either 30° C. or 50° C. for 30 minutes. After 30 minutes, the shaking was stopped and the phases were allowed to separate at their respective temperatures for 15 minutes. At this point, the aqueous layer was sampled and the acetate concentration was measured using a Dionex HPLC. Distribution coefficient (D) values were calculated as follows. $D=[HOAc]_{org}/[HOAc]_{Aq,f}$ where $[HOAc]_{org}=[HOAc]_{Aq\ initial}-[HOAc]_{Aq\ final}$. At 80° C. the extraction was carried out by submersing the flask containing the components detailed above in a pre-equilibrated water bath with magnetic stirring at 400 r.p.m. The results are shown in Table 1.

The most efficient extraction of acetic acid took place at 30° C., followed by 50° C. and 80° C. However, high D values were obtained at all three temperatures. The concentration of acetic acid in the solvent phase reached vales as high as 5% to 6% at all three temperatures. D increased with increasing acetic acid concentration to about 16 g/L then decreased upon further increases in acetic acid concentration.

TABLE 1

Effect of incubation temperature and acetic acid concentration on the extraction and distribution coefficient of acetic acid.

| Temperature | $HOAc_i$ (g/L, aq) | $HOAc_f$ (g/L, aq) | HOAc (g/L, org) | D, distribution coefficient |
|---|---|---|---|---|
| 30° C. | 5.63 | 0.06 | 5.57 | 93.02 |
|  | 12.08 | 0.09 | 12.00 | 138.20 |
|  | 16.95 | 0.10 | 16.85 | 172.18 |
|  | 32.89 | 0.30 | 32.58 | 107.71 |
|  | 61.41 | 11.05 | 50.36 | 4.56 |
|  | 96.90 | 36.03 | 60.87 | 1.69 |
| 50° C. | 5.42 | 0.06 | 5.36 | 98.20 |
|  | 11.26 | 0.085 | 11.18 | 131.25 |
|  | 16.26 | 0.10 | 16.15 | 154.69 |
|  | 31.37 | 0.54 | 30.84 | 57.69 |
|  | 52.50 | 9.25 | 43.25 | 4.68 |
|  | 86.71 | 34.51 | 52.19 | 1.51 |
| 80° C. | 5.42 | 0.16 | 5.25 | 41.35 |
|  | 11.26 | 0.37 | 10.89 | 32.21 |
|  | 16.26 | 0.72 | 15.54 | 69.36 |
|  | 31.37 | 2.50 | 28.88 | 11.56 |
|  | 52.50 | 12.29 | 40.22 | 3.27 |
|  | 86.71 | 34.36 | 52.35 | 1.52 |

Example 4

Liquid-liquid Extraction of Formic Acid with Alamine® 336 and Nonylphenol at Atmospheric Pressure This example shows that other volatile carboxylic acids besides acetic acid, such as formic acid, can be extracted using a high molecular weight amine plus a co-solvent (Table 2) from a dilute aqueous solution.

Five milliliters (5 mL) of an aqueous phase was used with a total extraction volume of 10 mL as detailed above in Example 3. The extractions were conducted in 25 mL Erlenmyer flasks in an incubator shaker and 400 r.p.m. at 30° C. for 30 minutes. After 30 minutes, the shaking was stopped and the phases were allowed to separate at their respective temperatures for 15 minutes. At this point, the aqueous layer was sampled and the formic acid concentration was measured using a Dionex HPLC. Distribution coefficients (D) were calculated as follows. $D=[HCO_2H]_{org}/[HCO_2H]_{Aq,f}$ where $[HCO_2H]_{org}=[HCO_2H]_{Aq\ initial}-[HCO_2H]_{Aq\ final}$. The extraction of formic acid by Alamine® 336 and nonylphenol is effective at concentrations as high as 25 g/L formic acid in the solvent phase.

TABLE 2

Effect of formic acid concentration on the extraction and distribution coefficient of formic acid by Alamine ® 336 and nonylphenol.

| $HCO_2H_i$ (g/L, aq) | $HCO_2H_f$ (g/L, aq) | $HCO_2H$ (g/L, solvent) | D distribution coefficient |
|---|---|---|---|
| 4.07 | 0.05 | 4.02 | 84.75 |
| 8.15 | 0.06 | 8.09 | 144.66 |
| 12.15 | 0.06 | 12.09 | 197.56 |
| 23.06 | 0.08 | 22.98 | 307.37 |
| 38.01 | 9.37 | 28.64 | 3.05 |
| 66.85 | 36.45 | 30.40 | 0.83 |

Example 5

Liquid-liquid Extraction of Acetic Acid with Various Amines

This example demonstrates that several combinations of amines (Table 3) and co-solvents (Table 4) may be used to extract acetic acid.

The extraction of acetic acid with the amine and co-solvent combinations was carried out as set forth in Example 4. The distribution coefficients were determined as set forth in Example 3.

The extraction of acetic acid is effective with nonylphenol co-solvent at acetic acid concentrations as high as 35 g/L in the solvent phase. The extraction of acetic acid is effective with naphthol co-solvent at a wide range of acetic acid concentrations.

TABLE 3

Effect of the amine on the extraction and distribution coefficient for acetic acid with nonylphenol co-solvent.

| $HOAc_i$ (g/L, aq) | amine:co-solvent | ratio | $HOAc_f$ (g/L, aq) | HOAc (g/L, solvent) | D distribution coefficient |
|---|---|---|---|---|---|
| 6.40 | $N(C_8)_3$ + $N(C_{10})_3$:nonylphenol | 15:15:70 | 0.07 | 6.33 | 96 |
| 33.8 | $N(C_8)_3$ + $N(C_{10})_3$:nonylphenol | 15:15:70 | 0.32 | 33.48 | 104.6 |
| 86.20 | $N(C_8)_3$ + $N(C_{10})_3$:nonylphenol | 15:15:70 | 38.9 | 47.30 | 1.2 |
| 5.79 | $N(C_6)_3$:nonylphenol | 30:70 | 0.18 | 5.61 | 31.60 |
| 34.71 | $N(C_6)_3$:nonylphenol | 30:70 | 0.46 | 34.25 | 65.35 |
| 100.85 | $N(C_6)_3$:nonylphenol | 30:70 | 21.28 | 79.57 | 3.74 |
| 5.29 | $N(C_{12})_3$:nonylphenol | 30:70 | 0.028 | 5.26 | 185.1 |
| 30.24 | $N(C_{12})_3$:nonylphenol | 30:70 | 0.143 | 30.10 | 210.88 |
| 83.75 | $N(C_{12})_3$:nonylphenol | 30:70 | 44.99 | 38.76 | 0.86 |

TABLE 4

Effect of the co-solvent on the extraction and distribution coefficient for acetic acid with Alamine ® 336.

| $HOAc_i$ (g/L, aq) | amine:co-solvent | ratio wt % | $HOAc_f$ (g/L, aq) | HOAc (g/L, solvent) | D distribution coefficient |
|---|---|---|---|---|---|
| 5.45 | Alamine ® 336:octanol | 30:70 | 0.53 | 4.92 | 9.22 |
| 29.18 | Alamine ® 336:octanol | 30:70 | 5.1 | 24.08 | 4.73 |
| 91.31 | Alamine ® 336:octanol | 30:70 | 25.87 | 65.44 | 2.53 |
| 6.01 | Alamine ® 336:2-napthol | 50:50* | 0.093 | 5.92 | 63.64 |
| 32.19 | Alamine ® 336:2-napthol | 50:50 | 0.20 | 31.99 | 161.05 |
| 95.94 | Alamine ® 336:2-naphthol | 50:50 | 4.71 | 91.23 | 19.37 |

*2-naphthol is a solid but can be dissolved in a 50:50 wt % mixture with alamine ® 336.

Example 6

Vapour Extraction of Acetic Acid

Referring to FIG. 2, the scrubber flask 3 containing 66 mL of scrubbing solution, i.e., organic solvent 4, which was a 30:70 mixture of Alamine® 336 and nonylphenol, was heated in a 135-140° C. oil bath (not shown) until the internal temperature of the scrubber flask reached 125° C. Simultaneously, the collection flask 5 was cooled to 0° C. in an ice-water bath. When the organic solvent 4, reached the target temperature, the feed flask 1, containing 66 mL of an aqueous 3.2% acetic acid solution (31.67 g/L, 2.1 g of acetic acid)₂, was then connected to scrubber flask 3 and heated using a 140° C. heating mantle. With heating, and after about 5 minutes, the vapour generated in the feed flask 1 was directed through the gas inlet tube 8 into the organic solvent 4 and bubbled through it. The organic phase temperature was maintained at 125-135° C. The glass adaptor 7 directs the vapor generated, after passing through the organic solvent 4, to gas inlet tube 9 and then into the cooled collection flask 5 where it condenses. After 60 minutes, 36 mL (containing 0.08 g acetic acid) of an aqueous solution was recovered in the collection flask 5 and 26 mL of liquid (48.39 g/L, 0.1.26 g acetic acid) remained in the feed flask 1. The apparatus was removed from the heating and cooling sources. The organic solvent in scrubber flask 3 was found to contain 9.66 g/L (0.64 g of acetic acid) using the base washing procedure described above. The glass adaptors were rinsed with a fixed amount of water to collect droplets of moisture that may contain acetic acid. The rinses contained 0.003 g of acetic acid. The acetic acid recovery was 76.5% of that evaporated from the feed.

TABLE 5

Vapour extraction of acetic acid

| Sample | Volume (mL) | g/L | g acetic acid |
|---|---|---|---|
| Feed flask, Initial | 66.0 | 31.67 | 2.1 |
| Feed flask, Final | 26.0 | 48.39 | 1.26 |

TABLE 5-continued

Vapour extraction of acetic acid

| Sample | Volume (mL) | g/L | g acetic acid |
|---|---|---|---|
| Total acetic acid evaporated | — | — | 0.84 |
| Rinse 1 | 7.1 | 0.09 | 0.002 |
| Rinse 2 | 6.4 | 0.26 | 0.001 |
| Acetic acid in organic solvent | 66.0 | 9.66 | 0.64 |
| Condensate in receiving flask | 36 | 2.4 | 0.08 |

Example 7

Recovery of Acetic Acid from the Organic Solvent by Distillation

Sixty six milliliters of organic solvent containing 0.64 g of acetic acid extracted from the vapour phase was heated to 200° C. in a 250 mL 3-neck round bottom flask. The oil bath temperature was set to 220° C. A distillation was conducted at ambient pressure using a 300 mm reflux condenser cooled with tap water and fitted to a 250 mL round bottom receiving flask. After 6 hrs the distillation was stopped. The concentration of acetic acid in the distillate was measured using a Dionex HPLC. The distillation glassware was rinsed to collect any droplets of moisture that may contain acetic acid. The results of the experiment are shown in Table 6. A total of 31.3% of the acetic acid was recovered in the distillate and the rinses.

TABLE 6

Recovery of acetic acid from the organic solvent

| Sample | Volume (mL) | g/L | g acetic acid | % of the acetic acid |
|---|---|---|---|---|
| Distillate | 0.72 | 152.06 | 0.11 | 17.15 |
| Rinse 1 | 17.5 | 2.73 | 0.048 | 7.48 |
| Rinse 2 | 10.43 | 4.14 | 0.043 | 6.70 |
| Total acetic acid recovered | — | — | — | 31.3 |
| Residual organic solvent | 66.0 | 4.84 | 0.32 | 67.04 |

The invention claimed is:

1. A process for recovering a volatile carboxylic acid from an aqueous stream containing same comprising the steps of:
   (a) evaporating the aqueous stream to produce a vapour stream comprising the volatile carboxylic acid that has been vapourized and water vapour, which aqueous stream is produced by a conversion process using a lignocellulosic feedstock comprising lignin as a substrate;
   (b) contacting the vapour stream with an organic solvent so as to extract the volatile carboxylic acid present in the vapour stream, thereby producing a liquid stream comprising the organic solvent and the volatile carboxylic acid, and a water vapour stream, wherein the organic solvent has an atmospheric boiling point of at least about 150° C. and is insoluble in water; and
   (c) separating the volatile carboxylic acid from the organic solvent.

2. The process of claim 1, wherein the volatile carboxylic acid is separated from the organic solvent by distillation.

3. The process of claim 2, wherein organic solvent obtained from the step of separating is reused in the process.

4. The process of claim 1, wherein in the step of contacting, the organic solvent comprises an aliphatic amine having at least 10 carbon atoms and a phenol, a naphthol or an alkylphenol having 1 to 40 carbon atoms in their alkyl group.

5. The process of claim 4, wherein the alkylphenol is nonylphenol or octylphenol.

6. The process of claim 4, wherein the aliphatic amine is selected from the group consisting of tributylamine, tripentylamine, trihexylamine, trioctylamine, tridecylamine and mixtures thereof.

7. The process of claim 1, wherein the lignocellulosic feedstock is selected from the group consisting of corn stover, soybean stover, corn cobs, rice straw, rice hulls, switch grass, corn fiber, wheat straw, barley straw, canola straw, oat straw, oat hulls and combinations thereof.

8. The process of claim 1, wherein the aqueous stream that is evaporated is a fermentation broth comprising a fermentation product produced by pretreating the lignocellulosic feedstock with acid or alkali so as to produce a pretreated feedstock composition comprising fiber solids containing cellulose, hydrolyzing the cellulose to glucose and then fermenting the glucose to produce the fermentation broth comprising the fermentation product.

9. A process for recovering a volatile carboxylic acid from an aqueous stream containing same comprising the steps of:
   (a) evaporating the aqueous stream to produce a vapour stream comprising the volatile carboxylic acid that has been vapourized and water vapour, which aqueous stream that is evaporated is a still bottoms stream produced by pretreating a lignocellulosic feedstock with acid or alkali so as to produce a pretreated feedstock composition comprising fiber solids containing cellulose, hydrolyzing the cellulose to glucose, fermenting the glucose to produce a fermented solution comprising ethanol and distilling the fermented solution to produce concentrated ethanol and the still bottoms stream;
   (b) contacting the vapour stream with an organic solvent so as to extract the volatile carboxylic acid present in the vapour stream, thereby producing a liquid stream comprising the organic solvent and the volatile carboxylic acid, and a water vapour stream, wherein the organic solvent has an atmospheric boiling point of at least about 150° C. and is insoluble in water; and
   (c) separating the volatile carboxylic acid from the organic solvent.

10. The process of claim 1, wherein the aqueous stream that is evaporated is a stream produced by hydrolyzing hemicellulose and cellulose present in the lignocellulosic feedstock with acid or alkali.

11. The process of claim 1, wherein the evaporating is conducted at a temperature of 40° C. to 145° C. and wherein the evaporating is operated at atmospheric pressure, under vacuum, at a pressure above atmospheric pressure or a combination thereof.

12. The process of claim 1, wherein the extracting is conducted at a temperature of about 60° C. to about 120° C. and wherein the extracting is operated at atmospheric pressure, under vacuum, at a pressure above atmospheric pressure or a combination thereof.

13. The process of claim 1, wherein the extracting is conducted at a temperature of about 60° C. to about 175° C. and wherein the extracting is operated at atmospheric pressure, under vacuum, at a pressure above atmospheric pressure or a combination thereof.

14. The process of claim 13, wherein the extracting is conducted at a temperature of about 60° C. to about 150° C. and wherein the extracting is operated at atmospheric pressure, under vacuum, at a pressure above atmospheric pressure or a combination thereof.

15. The process of claim 14, wherein the extracting is conducted at a temperature of about 60° C. to about 130° C. and wherein the extracting is operated at atmospheric pressure, under vacuum, at a pressure above atmospheric pressure or a combination thereof.

16. The process of claim 1, wherein the volatile carboxylic acid that is recovered is acetic acid.

17. The process of claim 1, wherein in the step of contacting, water is insoluble in the organic solvent.

18. The process of claim 1, wherein the volatile carboxylic acid that is present in the aqueous stream fed to the evaporating step is at a concentration of less than about 5 wt%.

19. A process for recovering a volatile carboxylic acid from an aqueous stream containing same comprising the steps of:
(a) evaporating the aqueous stream to produce a vapour stream comprising the volatile carboxylic acid that has been vapourized and water vapour, which aqueous stream is produced by a conversion process that comprises the steps of pretreating a lignocellulosic feedstock with acid or alkali to produce a pretreated feedstock composition comprising fiber solids containing cellulose, hydrolyzing the cellulose to glucose with cellulase enzymes and β-glucosidase and fermenting the glucose to ethanol or butanol;
(b) contacting the vapour stream with an organic solvent so as to extract the volatile carboxylic acid present in the vapour stream, thereby producing a liquid stream comprising the organic solvent and the volatile carboxylic acid, and a water vapour stream, wherein the organic solvent has an atmospheric boiling point of at least about 150° C. and is insoluble in water; and
(c) separating the volatile carboxylic acid from the organic solvent.

20. A process for recovering a volatile carboxylic acid from an aqueous stream containing same comprising the steps of:
(a) evaporating the aqueous stream to produce a vapour stream comprising the volatile carboxylic acid that has been vapourized and water vapour, which aqueous stream is produced by a conversion process that comprises the steps of pretreating a lignocellulosic feedstock with acid to produce a pretreated feedstock composition comprising fiber solids containing cellulose, hydrolyzing the cellulose to glucose with cellulase enzymes and β-glucosidase and fermenting the glucose to ethanol;
(b) contacting the vapour stream with an organic solvent so as to extract the volatile carboxylic acid present in the vapour stream, thereby producing a liquid stream comprising the organic solvent and the volatile carboxylic acid, and a water vapour stream, wherein the organic solvent has an atmospheric boiling point of at least about 150° C. and is insoluble in water; and
(c) separating the volatile carboxylic acid from the organic solvent.

21. A process for recovering a volatile carboxylic acid from an aqueous stream containing same comprising the steps of:
(a) evaporating the aqueous stream to produce a vapour stream comprising the volatile carboxylic acid that has been vapourized and water vapour, which aqueous stream is produced by a conversion process using a lignocellulosic feedstock as a substrate;
(b) contacting the vapour stream with an organic solvent having a distribution coefficient of at least 5 so as to extract the volatile carboxylic acid present in the vapour stream, thereby producing a liquid stream comprising the organic solvent and the volatile carboxylic acid, and a water vapour stream, wherein the organic solvent has an atmospheric boiling point of at least about 150° C. and is insoluble in water; and
(c) separating the volatile carboxylic acid from the organic solvent.

* * * * *